United States Patent [19]
McCormack et al.

[11] Patent Number: 5,955,187
[45] Date of Patent: Sep. 21, 1999

[54] MICROPOROUS FILM WITH LIQUID TRIGGERED BARRIER FEATURE

[75] Inventors: Ann Louise McCormack, Cumming; David Craige Strack, Canton; Jay Sheldon Shultz; William F. Cartwright, both of Roswell; Carol A. Blaney, Roswell, all of Ga.

[73] Assignee: Kimberly-Clark Worldwide, Inc., Neenah, Wis.

[21] Appl. No.: 08/962,611

[22] Filed: Oct. 31, 1997

Related U.S. Application Data

[63] Continuation-in-part of application No. 08/956,924, Oct. 23, 1997, which is a continuation of application No. 08/469,052, Jun. 6, 1995, abandoned.

[51] Int. Cl.[6] ........................................................ B32B 3/26
[52] U.S. Cl. ..................... 428/315.5; 428/315.7; 428/315.9; 428/316.6; 428/317.1; 428/317.9; 428/319.3; 428/913; 442/370; 442/372; 442/374
[58] Field of Search ................................ 428/213, 315.5, 428/315.7, 315.9, 316.6, 317.1, 317.9, 319.3, 326, 327, 330, 331, 913; 442/77, 370, 372, 374

[56] References Cited

U.S. PATENT DOCUMENTS

| | | |
|---|---|---|
| 3,654,929 | 4/1972 | Nilsson et al. . |
| 3,683,917 | 8/1972 | Comerford . |
| 4,318,408 | 3/1982 | Korpman . |
| 4,427,737 | 1/1984 | Cilento et al. ........................ 428/315.7 |
| 4,449,977 | 5/1984 | Korpman . |
| 4,472,328 | 9/1984 | Sugimoto et al. . |
| 4,585,604 | 4/1986 | Okuyama et al. . |
| 4,704,238 | 11/1987 | Okuyama et al. . |
| 4,793,956 | 12/1988 | Nogiwa et al. . |
| 4,814,124 | 3/1989 | Aoyama et al. . |
| 4,824,718 | 4/1989 | Hwang . |
| 4,877,679 | 10/1989 | Leatherman et al. . |
| 4,879,078 | 11/1989 | Antoon, Jr. . |
| 4,902,553 | 2/1990 | Hwang et al. . |
| 4,921,653 | 5/1990 | Aoyama et al. . |
| 5,167,652 | 12/1992 | Mueller . |
| 5,272,236 | 12/1993 | Lai et al. . |
| 5,317,035 | 5/1994 | Jacoby et al. . |
| 5,322,728 | 6/1994 | Davey et al. . |
| 5,447,788 | 9/1995 | Rhim et al. . |
| 5,472,775 | 12/1995 | Obijeski et al. . |
| 5,571,619 | 11/1996 | McAlpin et al. . |
| 5,580,910 | 12/1996 | Isaac et al. ................................ 529/17 |
| 5,695,868 | 12/1997 | McCormack ............................. 428/283 |
| 5,695,871 | 12/1997 | Tallentire et al. ..................... 428/320.2 |

FOREIGN PATENT DOCUMENTS

| | | |
|---|---|---|
| 1296225 | 2/1992 | Canada . |
| 0604731 | 7/1994 | European Pat. Off. . |
| 9516562 | 6/1995 | WIPO . |
| 96/19346 | 6/1996 | WIPO . |
| 96/39032 | 12/1996 | WIPO . |
| 98/29247 | 7/1998 | WIPO . |

OTHER PUBLICATIONS

The Merck Index, Encyclopedia of Chemicals and Drugs, Eighth Edition (Dec. 1968), p. 126.

*Primary Examiner*—Blaine Copenheaver
*Attorney, Agent, or Firm*—Pauley Petersen Kinne & Fejer

[57] ABSTRACT

A self-regulating breathable microporous film layer transmits water vapor at normal use conditions, and reduces or eliminates the vapor transmission when the vapor in the environment becomes excessive. The film layer includes a voided polymer matrix and a plurality of fine water-swellable filler particles disposed within the voids. When there is an excess of vapor, the filler particles swell to block or partially block transmission of vapor through the voids and the film layer.

59 Claims, 4 Drawing Sheets

MICROPOROUS FILM WITH LIQUID TRIGGERED BARRIER FEATURE

RELATED U.S. APPLICATION

This is a continuation-in-part application of U.S. patent application Ser. No. 08/956,924 filed Oct. 23, 1997, filed in the name of Blaney et al., now pending, which is a continuation of U.S. patent application Ser. No. 08/469,052 filed Jun. 6, 1995, now abandoned, the entire contents of the aforesaid application are incorporated herein by reference.

FIELD OF THE INVENTION

The present invention is a breathable voided microporous film containing a particulate filler which swells inside the voids when wet, thereby enhancing the barrier features. The invention includes both monolayer and multilayer films.

BACKGROUND OF THE INVENTION

Vapor permeable, liquid impermeable polymeric films are known in the art. One method of making a polymeric film vapor permeable, involves mixing a matrix polymer with a substantial quantity (e.g. 10–70% by weight) of an organic or inorganic particulate filler such as, for example, calcium carbonate, and extruding a film from the blend. The matrix polymer may include a polyolefin, such as polyethylene or polypropylene, or various olefin copolymers. The film may be a monolayer film, a multilayer film which contains the filled layer as a primary layer, or a multilayer film having more than one filled layer.

Then, the film is heated and stretched, causing voids to form in the areas surrounding the filler particles. The voided film is characterized by thin polymer membranes and/or fine pore networks which permit the molecular diffusion of water vapor through the film, but which block the passage of liquids. In essence, a tortuous path is created from one film surface to the other which permits transfer of vapors but not liquids.

Breathable films are employed in backsheets, for example as a backsheet component laminated to a nonwoven web and/or other layers, in many of today's personal care absorbent articles. Diapers are one example. Filled, stretched polyolefin films provide good water vapor transmission, making the diapers more comfortable to the wearer. As a result, the relative humidity and temperature within the diaper or other product can be reduced by using breathable films and laminates. Despite this, breathable films have the disadvantage of being cold and clammy to the touch, because moisture which passes through the films condenses readily on the outer surface. Accordingly, when nonwoven webs are laminated to the films, the laminates are placed with the film on the inside (diaper facing side) and the nonwoven web on the outside of the laminate.

Even with the use of nonwoven layers, a wet feeling may develop as the condensed moisture from the film penetrates the adjacent nonwoven layer. There is a need or desire for a breathable film useful in a backsheet for absorbent articles which exhibits increased barrier when the film surface gets wet.

Breathable films are also used in surgical gowns. Again, the objective is to provide good water vapor transmission and make the gowns comfortable to the wearer. However, if a gown is too breathable, it may be less effective in providing barrier when exposed to an insult from a potentially contaminated liquid, such as blood. For surgical gowns, there is a need or desire for a breathable film which exhibits increased barrier to pressure induced penetration when exposed to a liquid insult.

SUMMARY OF THE INVENTION

The present invention is a self-regulating breathable microporous film layer which is generally permeable to vapor and impermeable to liquids, and which becomes less permeable or impermeable to vapor and pressure-induced liquid penetration when wet. The invention is particularly useful as an outercover material for personal care disposable products such as diapers, training pants, and adult incontinence products. The invention is also useful for breathable surgical gowns, and other breathable applications.

The self-regulating film layer of the invention includes a polymer matrix component and a water-swellable filler component. The polymer matrix preferably includes a polyolefin, and constitutes about 30–90% by weight of the film layer. The self-regulating film layer also includes a water-swellable filler component. The water-swellable filler may be an organic or inorganic filler, and constitutes about 10–70% by weight of the film layer.

The self-regulating film layer may include a conventional (i.e. non-water-swellable) particulate filler in addition to the water-swellable filler. The total amount of filler, including swellable and non-swellable filler, should be about 10–70% by weight of the film layer. The fillers may be combined in any desired ratio depending on the amount of self-regulation desired.

The filler(s) and polymer matrix component are initially melt blended, and the blend is extruded into a precursor film layer. The precursor film layer may be extruded as a single-layer film, or may constitute one or more layers in a multilayer film structure. The film is then stretched at an elevated temperature below the melting temperature of the polymer component. As the film is stretched, voids form around the filler particles to form a microporous, breathable self-regulating film layer.

The self-regulating film layer functions as a typical microporous breathable film during times of low to moderate moisture exposure. The voided film is characterized by thin polymer membranes surrounding the filler particles, and/or fine pore networks, either of which creates a tortuous path so that the film allows the molecular diffusion of water vapor through the film, but does not allow penetration by liquid water. When the vapor penetration becomes excessive, such as when one side of the film is exposed to a saturated or otherwise high vapor concentration or an aqueous liquid, the water-swellable filler particles become wet from condensation and begin to swell, filling the voids to various degrees. By this mechanism, the vapor permeable tortuous paths are reduced or closed off.

With the foregoing in mind, it is a feature and advantage of the invention to provide a self-regulating breathable, microporous film layer which transmits water vapor, but which acts as a flow regulator to reduce or prevent passage of vapor levels or liquid from one film side that are high enough to cause the opposing film side to feel wet and clammy.

It is also a feature and advantage of the invention to provide a self-regulating, breathable microporous film which exhibits a regional increase in moisture and liquid barrier, without affecting breathability in other areas, when only a region is exposed to high vapor levels or an aqueous liquid.

It is also a feature and advantage of the invention to provide a breathable multilayer film which includes at least one self-regulating film layer.

It is also a feature and advantage of the invention to provide a film/nonwoven laminate useful in personal care products, surgical gowns and the like, in which the film includes at least one self-regulating layer.

The foregoing and other features and advantages will become further apparent from the following detailed description of the presently preferred embodiments, read in conjunction with the accompanying examples and drawings.

The detailed description, examples and drawings are merely illustrative rather than limiting, the scope of the invention being defined by the appended claims and equivalents thereof.

TEST PROCEDURE

The following procedure is described for testing of the moisture vapor transmission rate (MVTR) or water vapor transmission rate (WVTR) for the self-regulating films of the present invention. WVTR for the sample materials was calculated in accordance with ASTM Standard E96-80. Circular samples measuring three inches in diameter were cut from each of the test materials and a control which was a piece of CELGARD™ 2500 film from Hoechst Celanese Corporation of Sommerville, N.J. CELGARD™ 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) or 1 hour to equilibrate. The oven was a constant temperature oven with external air circulating through it to prevent water vapor accumulation inside. A suitable forced air oven is, for example, a Blue M Power-O-Matic 60 oven distributed by Blue M. Electric Company of Blue Island, Ill. Upon completion of the equilibration, the pans were removed from the oven, weighed an immediately returned to the oven. After 24 hours, the pans were removed from the oven and weighed again. The preliminary test water vapor transmission rate values were calculated with Equation (I) below:

Test WVTR=(grams weight loss over 24 hours)×315.5 g/m$^2$/24 hours (I)

The relative humidity within the oven was not specifically controlled.

Under the predetermined set conditions of 100° F. (32° C.) and ambient relative humidity, the WVTR for the CELGARDT™ 2500 control has been defined to be 5000 grams per square meter for 24 hours. Accordingly, the control sample was run with each test and the preliminary test values were corrected to set conditions using Equation (II) below:

WVTR=(Test WVTR/control WVTR)×(5000 g/m$^2$/24 hours) (II)

The above procedure is useful for measuring the MVTR of "dry" self-regulating films in which the filler particles are not swollen. To measure the MVTR of "wet" self-regulating films, in which the filler particles are swollen, an initially dry film is treated with distilled water at 60 millibars pressure, at 37° C., for 2.5 hours. If the film is a multilayer film, the self-regulating layer should face towards the water. Following the water treatment, the film is then tested using the above procedure.

DETAILED DESCRIPTION OF THE PRESENTLY PREFERRED EMBODIMENTS

Figure 1:
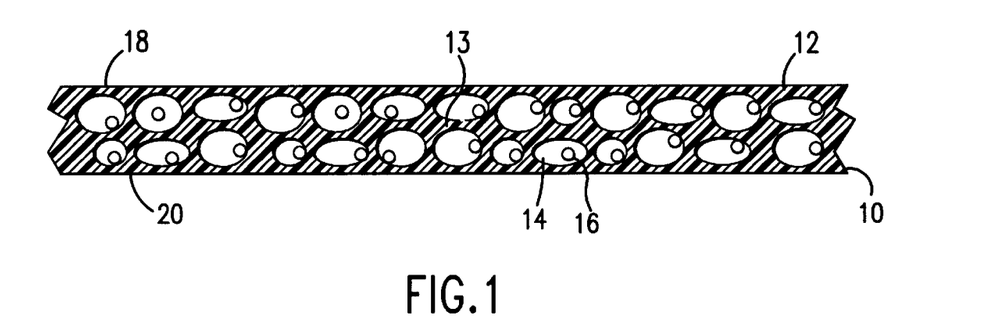
FIG. 1 is a cross-sectional view of a self-regulating film layer in which the filler particles are in the dry (unswollen) state.

Referring to FIG. 1, a self-regulating film layer 10 is shown including a polymer matrix 12, a plurality of voids 14 within the matrix surrounded by relatively thin microporous membranes 13 defining tortuous paths, and one or more water-swellable filler particles 16 (shown in the unswollen state) in each void 14. The film 10 is microporous and breathable, wherein the microporous membranes 13 between the voids readily permit molecular diffusion of water vapor from a first surface 18 to a second surface 20 of the film layer 10.

The polymer matrix 12 can be formed from any suitable film-forming thermoplastic polymer. Examples of suitable polymers include without limitation polyethylene, polypropylene, copolymers of mainly ethylene and $C_3$–$C_{12}$ alpha-olefins (commonly known as linear low density polyethylene), copolymers of mainly propylene with ethylene and/or $C_4$–$C_{12}$ alpha-olefins, and flexible polyolefins including propylene-based polymers having both atactic and isotactic propylene groups in the main polypropylene chain. Other suitable matrix polymers include without limitation elastomers, for example polyurethanes, copolyether esters, polyamide polyether block copolymers, ethylene vinyl acetate copolymers, block copolymers having the general formula A–B–A' or A–B such as copoly (styrene/ethylene-butylene), styrene-poly (ethylene-propylene)-styrene, styrene-poly (ethylene-butylene)-styrene, polystyrene/poly (ethylene-butylene)/polystyrene, poly (styrene/ethylene-butylene/styrene), and the like. Metallocene-catalyzed polyolefins are also useful, including those described in U.S. Pat. Nos. 5,571,619 to McAlpin et al.; 5,322,728 to Davis et al.; 5,472,775 to Obijeski et al.; and 5,272,236 to Lai et al., the disclosures of which are incorporated herein by reference.

Polymers made using metallocene catalysts have a very narrow molecular weight range. Polydispersity numbers (Mw/Mn) of below 4 and even below 2 are possible for metallocene-produced polymers. These polymers also have a controlled short chain branching distribution compared to otherwise similar Ziegler-Natta produced type polymers. It is also possible using a metallocene and/or constrained geometry catalyst system to control the molecular weight distribution and/or isotacticity of the polymer quite closely.

Commercial production of metallocene polymers is growing and such polymers are available from Exxon Chemical Company of Baytown, Tex. under the trade name ACHIEVE™ for polypropylene based polymers and EXACT™ and EXCEED™ for polyethylene based polymers. Dow Chemical Company of Midland, Mich. has polymers commercially available under the name ENGAGE™. These materials are believed to be produced using non-stereo selective metallocene catalysts. Exxon generally refers to their metallocene catalyst technology as "single site"0 catalyst while Dow refers to theirs as "constrained geometry" catalysts under the name INSIGHT™ to distinguish them from traditional Ziegler-Natta catalysts which have multiple reaction sites. Other manufacturers such as Fina Oil, BASF, Amoco, Hoechst and Mobil are active in this area and it is believed that the availability of polymers produced according to this technology will grow substantially in the next decade. In the practice of the instant invention, elastic polyolefins like polypropylene and polyethylene are also believed suitable to use with the present invention.

The polymer matrix should constitute about 30–90% by weight of the self-regulating film layer, preferably about 35–75% by weight, most preferably about 40–60% by weight.

The water-swellable filler particles 16 can include any water-swellable organic or inorganic filler. By "water-swellable" it is meant that the particles must be capable of absorbing at least about 5 times their weight, preferably at least about 10 times their weight, most preferably at least about 20 or 30 times their weight, in distilled water. Examples of organic water-swellable fillers include without limitation natural and synthetic superabsorbent materials. Natural superabsorbent materials include guar gum, agar, pectin and the like. Synthetic superabsorbent materials include synthetic silicas, hydrogel polymers such as alkali metal salts of polyacrylic acids, polyacrylamides, polyvinyl alcohol, ethylene-maleic anhydride copolymers, polyvinyl ethers, methyl cellulose, carboxymethyl cellulose, hydroxypropylcellulose, polyvinylmorpholinone, and polymers and copolymers of vinyl sulfonic acid, polyacrylates, polyacrylamides, polyvinylpyrridine, and the like. Other suitable polymers include hydrolyzed acrylonitrile grafted starch, acrylic acid grafted starch, and isobutylene maleic anhydride polymers and mixtures thereof. The hydrogel polymers are preferably lightly crosslinked to render the materials substantially water insoluble. Crosslinking may, for example, be accomplished by irradiation or by covalent, ionic, van der Waals, or hydrogen bonding. An example of a suitable commercially available superabsorbent is SAN-WET IM 3900 available from Hoechst Celanese located in Portsmouth, Va. and DRYTECH 2035LD available from Dow Chemical Co. located in Midland, Mich. Examples of inorganic water-swellable fillers include bentonite clays as well as other water-swellable clays. A suitable inorganic water-swellable filler is sodium bentonite clay having a mean particle size of about 1.0 micron. Sodium bentonite clay is an alkaline version of bentonite, which is a colloidal hydrated aluminum silicate clay found in the Midwest of the U.S.A. and Canada. Bentonite clay primarily includes montmorillonite having the approximate formula $Al_2O_3 \cdot 4SiO_2 \cdot H_2O$. Often the clays also contain Al, Mg, Na, Si and/or O although other elements may be present.

The polymer composition, filler content, filler particle size and degree of stretching are factors which help determine the breathability of the microporous film layer 10. Generally, the self-regulating film layer 10 will be less than about 50 microns thick, preferably less than about 30 microns thick, most preferably less than about 20 microns thick.

The filler content and degree of stretching affect the number of voids and the nature of the tortuous paths between the voids. The total filler content should range from about 10–70% by weight of the film layer 10, preferably about 25–65% by weight of the film layer 10, most preferably about 40–60% by weight of the film layer 10. The filler may comprise only swellable filler particles, or may include a mixture of swellable and nonswellable filler particles. The film may be uniaxially or biaxially stretched. The film may be uniaxially stretched to about 1.1–7.0 times its original length, preferably to about 1.5–6.0 times its original length, most preferably to about 2.5–5.0 times its original length. The film may alternatively be biaxially stretched using conventional techniques familiar to persons skilled in the art.

The filler particles 16 are preferably small, in order to maximize vapor transmission through the voids. Generally, the filler particles (in the dry unswollen state) should have a mean particle diameter of about 0.1–7.0 microns, preferably about 0.5–7.0 microns, most preferably about 0.8–2.0 microns. When non-swellable fillers are also added to the layer 10, as described below, the same particle size ranges are applicable.

Figure 2:
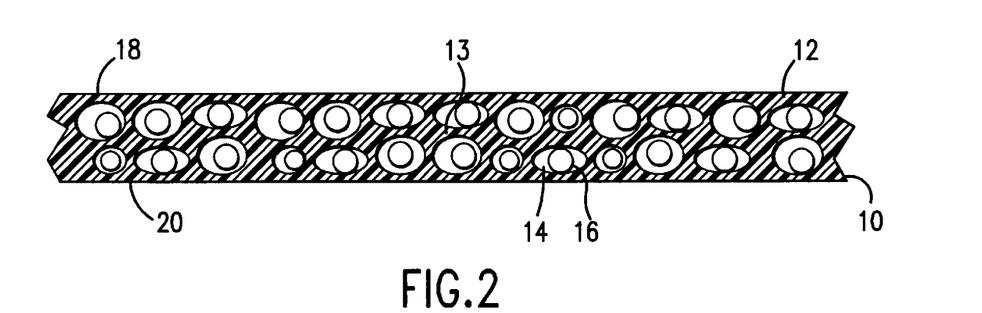
FIG. 2 is a cross-sectional view of a self-regulating film layer in which the filler particles are in the wet (swollen) state.

FIG. 2 shows the swellable filler particles 16 in their expanded state, after the film 10 has been exposed to liquid water or an excess of vapor which causes the particles to become wet. Swelling of the particles may result from various mechanisms depending on the film configuration. Contact of the breathable film with an aqueous liquid may cause the particles 16 to swell, if the layer 10 is positioned adjacent to the liquid insult. An excess of vapor may cause swelling if there is condensation on the layer 10. The excess of vapor may, for example, be caused by a wet diaper which, combined with the body's heat, creates vapor saturation on one side of the film layer 10. As shown in FIG. 2, the particles 16 swell to a state which partially or totally obstructs passage of further vapor through the voids 16. If the film layer 10 is only partly exposed to a liquid insult, or to condensation, then only that region of the layer 10 will experience swelling of the filler particles 16.

Figure 3:
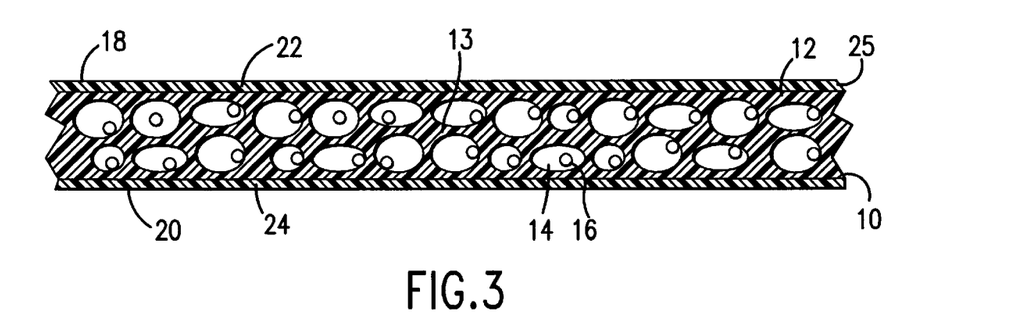
FIG. 3 is a cross-sectional view of a multilayer film including a self-regulating film layer as the core layer.

In the embodiment of FIG. 3, the self-regulating layer 10 is sandwiched between two relatively thin outer skin layer 22 and 24, in a multilayer film 25. The inclusion of skin layers improves film processability and can also contribute heat seal properties to the overall film 25. The multilayer film 25 can be prepared by cast or blown film coextrusion of the layers, by extrusion coating, or by any conventional layering process. The polymers in the outer layers 22 and 24 can be the same or different than the polymers in the self-regulating layer 10. Preferably, the polymers in the outer layer or layers have a lower softening point than in the self-regulating layer 10, and contribute to the heat sealability of the film 25.

Also, the thickness and composition of the outer layers can be selected so as not to substantially impair the moisture transmission through the breathable layer 10. This way, the breathable layer 10 may determine the breathability of the entire film, and the self-regulating feature of layer 10 may reduce or block the breathability of the film. To this end, the skin layers 22 and 24 are often less than about 30 microns thick, and desirably less than about 10 microns thick. Preferred skin layer polymers and/or copolymers include ethylene vinyl acetate, propylene vinyl acetate, ethylene methyl acrylate, other water vapor-permeable polymers, and blends of these with other polyolefins.

Figure 4:
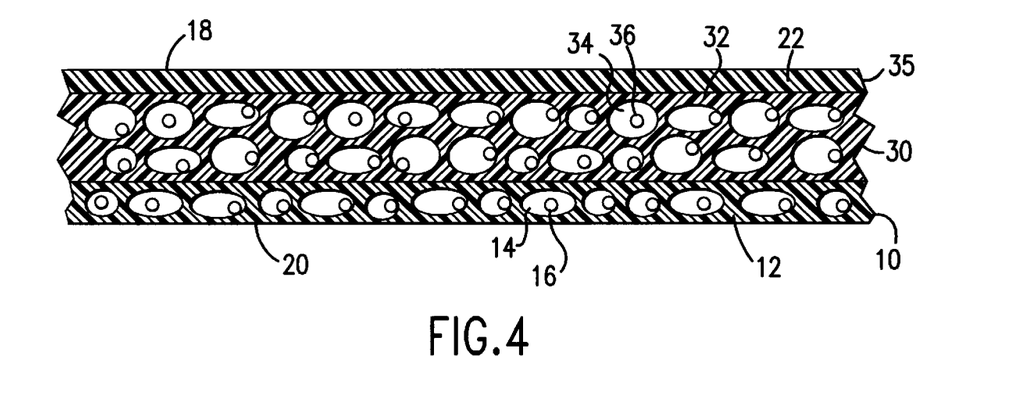
FIG. 4 is a cross-sectional view of a multilayer film including a self-regulating film layer as an outer skin layer.

FIG. 4 illustrates a multilayer film 35 in which the self-regulating film 10 is an external layer. The film 35 includes an inner core layer 30 which is a breathable microporous layer containing non-swellable filler particles 36 in the voids 34. In the film 35, an excess of vapor passing from a first side 18 to a second side 20 of the film and condensing will cause swelling of only the particles in the external layer 10, which is where the swelling and sealing is most needed to prevent the surface 20 from having a wet and clammy feel. The layer 22 of film 30 may have the same ranges of properties and limitations as the layer 22 in FIG. 3 described above. However, the layers 30 and 10 are not so limited, and may have the same or different thicknesses and the same or different matrix polymers.

The non-swellable filler particles 36 in core layer 30 may be selected from a wide variety of organic and inorganic fillers. Suitable non-swellable fillers include, but are not limited to, calcium carbonate, non-swellable clays, silica, alumina, barium sulfate, talc, magnesium sulfate, titanium dioxide, zeolites, aluminum sulfate, diatomaceous earth, magnesium carbonate, barium carbonate, kaolin, mica, carbon, magnesium oxide, aluminum hydroxide and non-swellable polymer particles. The preferred size ranges for the non-swellable particles 36 are the same as those described above for the swellable particles 16 in the dry state.

The non-swellable particles 36 in the films of the invention may be coated with a minor quantity (e.g. up to 2% by weight) of a fatty acid or other material to ease their dispersion in the polymer matrix. Suitable fatty acids include without limitation stearic acid, or a larger chain fatty acid such as behenic acid. In addition, the swellable particles 16 can optionally be coated with a water soluble or hydrophilic coating.

The amount of non-swellable filler 36 in the layer 30 should range from about 10–70% by weight of the layer 30, preferably about 25–65% by weight, most preferably about 40–60% by weight. When the self-regulating layer 10 is used as an external layer as in FIG. 4, the amount of swellable filler 16 may be the same or somewhat lower, preferably about 10–50% by weight of the external layer 10, most preferably about 15–30% by weight. If the multilayer film of FIG. 4 is used as a diaper backing, the self-regulating layer 10 should preferably face inward toward the absorbent core of the diaper, to permit immediate contact with a liquid insult. If the multilayer film is used in a surgical gown, the self-regulating layer 10 preferably faces the outside, permitting immediate contact with a blood splash or other external liquid insult.

Figure 5:
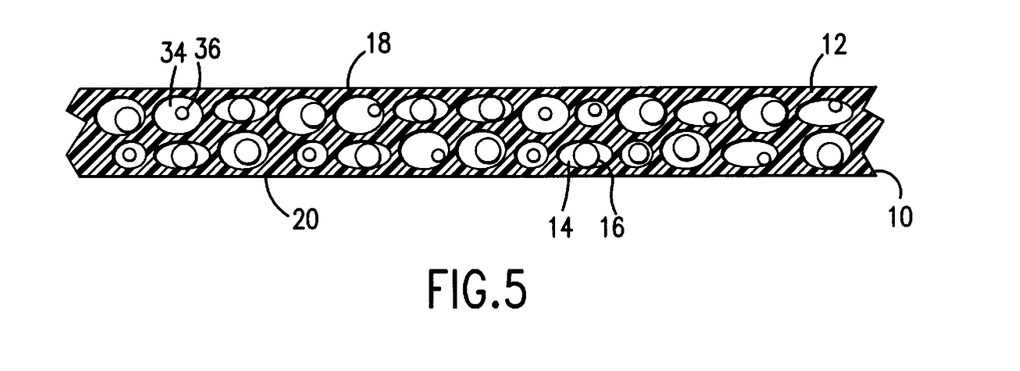
FIG. 5 is a cross-sectional view of a self-regulating film layer in which only some of the filler particles are water-swellable.

FIG. 5 illustrates an embodiment in which swellable filler particles 16 and non-swellable filler particles 36 are both contained in the same polymer matrix 12. By adding swellable and non-swellable filler particles into the same matrix layer, the self-regulating feature of the film layer 10 may itself be adjusted to provide whatever degree of blockage is needed when the film is contacted with condensed moisture vapor or a liquid insult. In the layer 10 of FIG. 5, the amount of total filler should be about 10–70% by weight of the layer 10, preferably about 25–65% by weight, most preferably about 40–60% by weight. The weight ratio of swellable to non-swellable filler can be between 9:1 and 1:9, or between 7:3 and 3:7, or whatever ratio is desirable.

Figure 6:
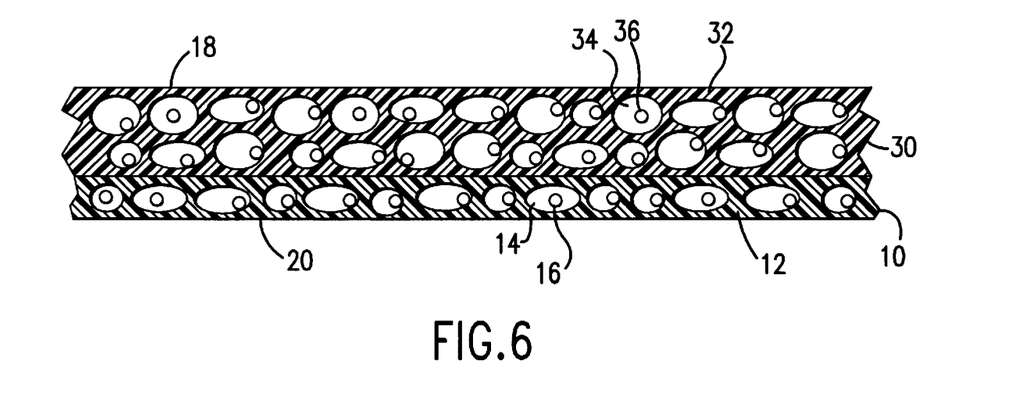
FIG. 6 is a cross-sectional view of a two-layer film including a filled self-regulating layer and a filled non-self-regulating layer.

FIG. 6 illustrates a two-layer film embodiment including a first thicker layer 30 and a second thinner layer 10. The thicker layer 30 is a breathable microporous layer containing a voided polyolefin matrix 32 having non-swellable filler particles 36 in the voids 34. The thinner layer 10 is a breathable microporous layer containing a voided polyolefin matrix 12 having swellable filler particles 16 in the voids 14. In a preferred embodiment, the non-swellable filler 36 includes particles of calcium carbonate, and the swellable filler 16 includes particles of a superabsorbent polymer. The amounts of the respective fillers in the layers 30 and 10 may be the same as described above with respect to FIG. 4.

Regardless of whether the self-regulating layer 10 is a monolayer film or a constituent of a multilayer film, the overall film should be constructed to function as a breathable microporous film, at least when the layer 10 is in the dry state. When the layer 10 is dry, the overall film should have a moisture vapor transmission rate (MVTR) or water vapor transmission rate (WVTR) of at least about 300 grams/m$^2$/24 hours measured using the procedure described above. Preferably, the overall film should have an WVTR of at least about 1200 grams/m$^2$/24 hours, most preferably at least 2000 grams/m$^2$/24 hours. When the film layer 10 becomes wet (i.e. the filler particles 16 swell), the overall film WVTR should fall to about 70% or less of its original value, and will preferably fall to about 50% or even about 25% or less of its original value. In some applications such as surgical gowns, it may be desirable for the overall film WVTR to drop to virtually zero when the layer 10 is exposed to a liquid insult, in order to maximize the total barrier properties of the gown. This can be accomplished through proper selection of swellable filler type and amount, and by placing the self-regulating layer 10 to face outward from the gown.

Figure 7:
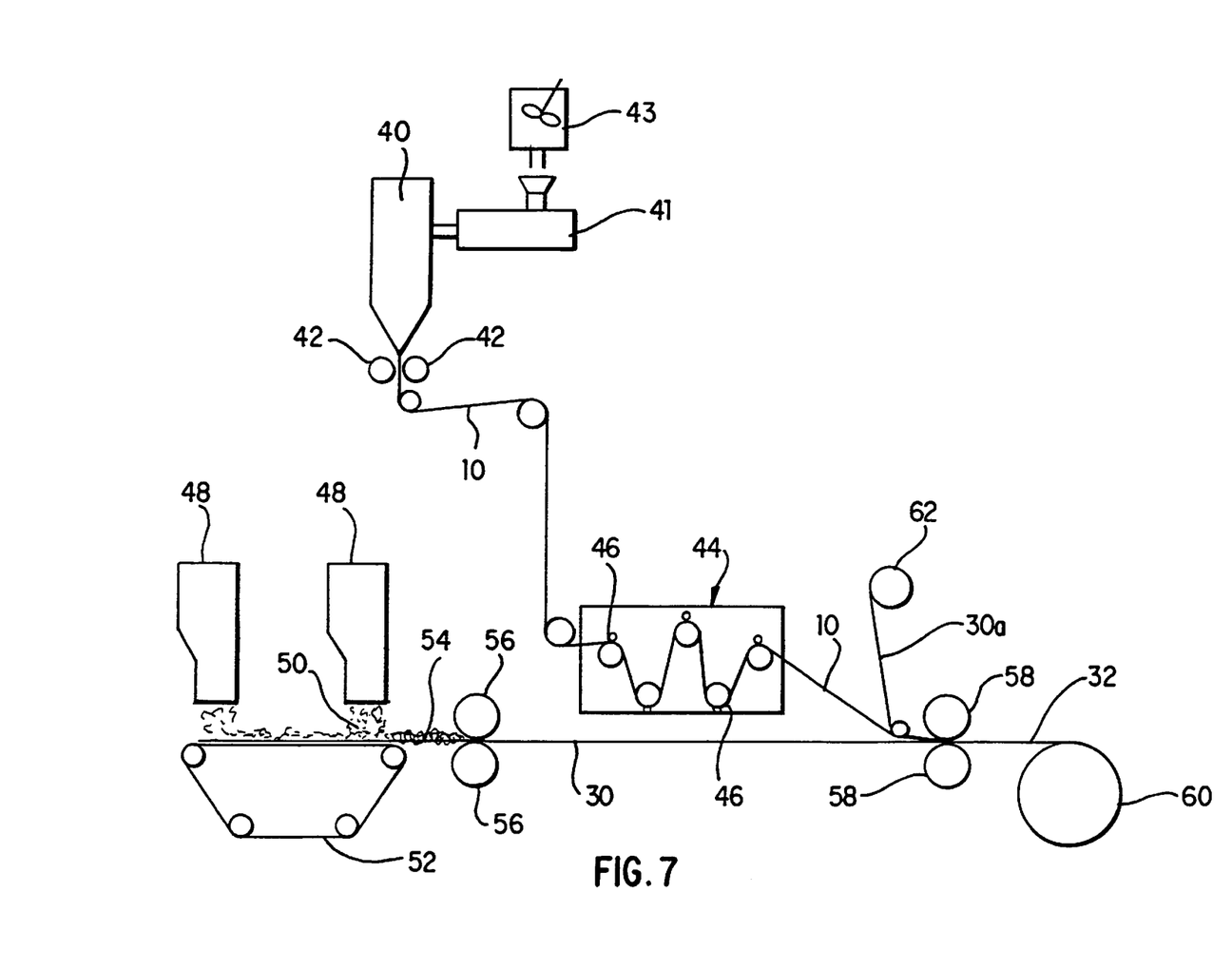
FIG. 7 is a schematic diagram of a process for making a self-regulating film and laminate.

FIG. 7 illustrates a process for forming a self-regulating microporous film or film layer. Referring to FIG. 7, film 10 is formed from a film extrusion apparatus 40 such as a cast or blown unit which could be in-line or off-line. Typically the apparatus 40 will include an extruder 41. Filled resin including the polymer matrix material and filler is prepared in a mixer 43 and directed to extruder 41. The film 10 is extruded into a pair of nip or chill rollers 42, one of which may be patterned so as to impart an embossed pattern to the newly formed film 10.

From the film extrusion apparatus 40 or off-line rolls supplied, the filled film 10 is directed to a film stretching unit 44 which can be a machine direction orienter, commercially available from vendors including the Marshall and Williams Co. of Providence, R.I. Apparatus 44 has a plurality of pairs of stretching rollers 46, with each subsequent pair moving at progressively faster speed than the preceding pair. The rollers 46 apply an amount of stress and progressively stretch the filled film 10 to a stretched length where the film 10 becomes microporous and breathable. As shown, the film 10 is stretched only in the machine direction, which is the direction of travel of the film 10 through the process in FIG. 7.

Advantageously, the film 10 may be uniaxially stretched to about three times its original length, using an elevated stretch temperature of about 150–200° F. for most polyolefin-based films. The elevated stretch temperature can be sustained by heating some of the stretch rollers 46. The optimum stretch temperature varies with the type of matrix polymer in the film 10, and is below the melting temperature of the matrix polymer.

Figure 8:
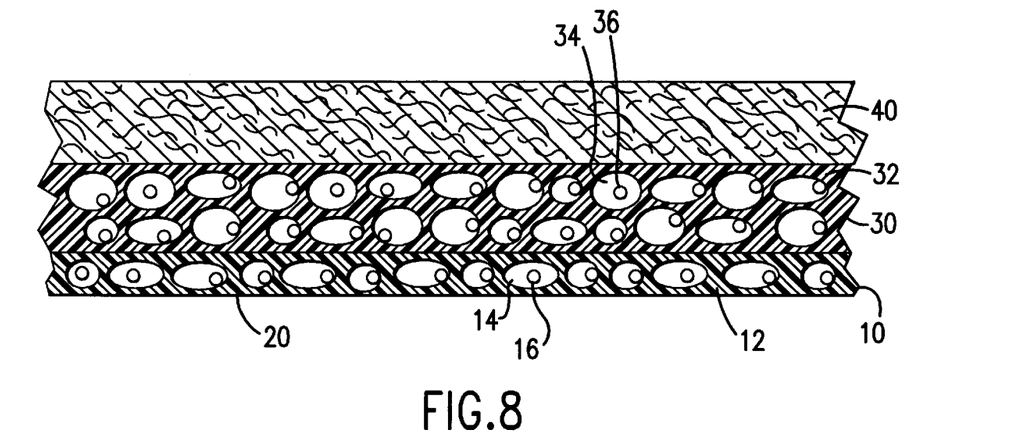
FIG. 8 is a cross-sectional view of a laminate including a nonwoven web and a two-layer film of FIG. 6.
Figure 9:
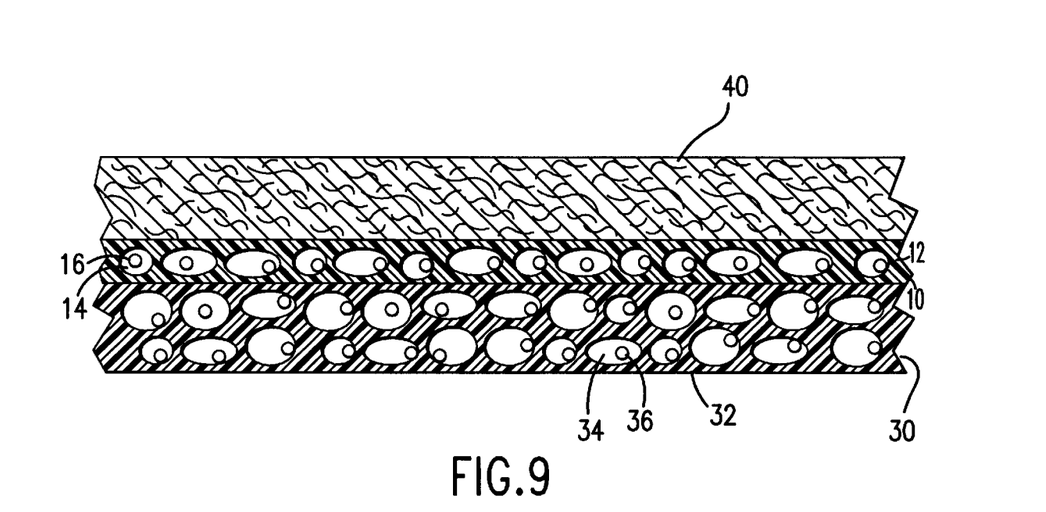
FIG. 9 is a cross-sectional view of another laminate including a nonwoven web and a two-layer self-regulating film.

The self-regulating film may be laminated to one or more substrates, such as a nonwoven web, using conventional adhesive bonding or thermal bonding techniques known in the art. The type of substrate and bonding will vary depending on the particular end use application. An example of a laminate is shown in FIG. 8, wherein a nonwoven web 40 is laminated to the multilayer film of FIG. 6. In the embodiment shown, the web 40, which can be a spunbonded web of polypropylene or polyethylene, is bonded to the voided film layer 32 of the multilayer film 30, which layer contains the non-swellable filler particles. The self-regulating layer 10 faces away from the nonwoven web 40. In one embodiment, the self-regulating layer 10 can face inward toward the absorbent core, while the nonwoven layer 40 would be exposed on the outside of the diaper. In still a further embodiment and in reference to FIG. 9, the self-regulating layer 10 is positioned between nonwoven web 40 and voided film layer 32. Desirably, such as in a diaper backing, the nonwoven web 40 would face away from the absorbent core of the diaper such that condensation formed on the diaper backing forms upon self-regulating layer 10.

Referring again to FIG. 7, the film 10 may be laminated to nonwoven web 30 immediately after the film is stretched and immediately following manufacture of the nonwoven web. The nonwoven web 30, which can be a spunbonded web, is formed by dispensing polymer filaments 50 from a pair of conventional spinnerettes 48, onto a conveyor assembly 52. The filaments 50 are deposited onto the conveyor to form mat 54. The filaments 50 of mat 54 are then compressed to form inter-filament bonding using a pair of nip rollers 56, resulting in the spunbonded web 30. The spunbonded web 30 is then transported to the calender bonding rollers 58 and it thermally bonded to one side of the film 10. The film 10 in FIG. 7 is simultaneously bonded on its other side to a second material 30a originating from a supply roll 62. The second material 30a may be a second nonwoven web, or another film layer. The resulting laminate 32 is wound and stored onto a supply roll 60.

Other examples of laminates and end uses in which the self-regulating film may be useful are described in various patents and patent applications assigned to the Kimberly-Clark Worldwide, Inc. These include without limitation U.S. application Ser. No. 08/359,986, filed Dec. 20, 1994; U.S. application Ser. No. 08/755,692, filed Nov. 25, 1996; and U.S. application Ser. No. 08/777,365, filed Dec. 27, 1996. These patent applications are incorporated herein by reference in their entirety.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalents are intended to be embraced therein.

We claim:

1. A self-regulating microporous breathable film layer, comprising:
    about 30–90% by weight of a voided polymer matrix; and
    about 10–70% of a filler dispersed in the voided polymer matrix, the filler including a water-swellable filler selected from the group consisting of organic fillers, bentonite fillers and combinations thereof;
    the water-swellable filler having a dry unswollen state and a wet swollen state;
    the film having an original WVTR of at least about 300 grams/m$^2$/24 hours when the water-swellable filler is in the unswollen state and an WVTR less than about 70% of the original WVTR when the water-swellable filler is in the swollen state.

2. The self-regulating film layer of claim 1, wherein the water-swellable filler comprises an organic filler.

3. The self-regulating film layer of claim 2, wherein the organic filler comprises a superabsorbent polymer.

4. The self-regulating film layer of claim 1, wherein the inorganic filler comprises sodium bentonite clay.

5. The self-regulating film layer of claim 1, wherein the water-swellable filler has a mean particle diameter of about 0.1–7.0 microns in the unswollen state.

6. The self-regulating film layer of claim 1, wherein the water-swellable filler has a mean particle diameter of about 0.5–7.0 microns in the unswollen state.

7. The self-regulating film layer of claim 1, comprising about 35–75% by weight of the voided polymer matrix and about 25–65% by weight of the filler.

8. The self-regulating film layer of claim 1, comprising about 40–60% by weight of the voided polymer matrix and about 40–60% by weight of the filler.

9. The self-regulating film layer of claim 1, wherein the voided polymer matrix comprises a film-forming thermoplastic polymer.

10. The self-regulating film layer of claim 1, having a thickness less than about 50 microns.

11. The self-regulating film layer of claim 1, having a thickness less than about 30 microns.

12. The self-regulating film layer of claim 1, having a thickness less than about 20 microns.

13. The self-regulating film of claim 1 wherein the WVTR is less than 50% of the original WVTR when the water-swellable filler is in a wet swollen state.

14. A self-regulating microporous breathable film layer, comprising:
    about 30–90% by weight of a voided polyolefin matrix, and
    about 10–70% by weight of a filler dispersed in the polymer matrix, the filler including at least one water-swellable filler selected from the group consisting of organic fillers, bentonite fillers and combinations thereof, and at least one non-water-swellable filler.

15. The self-regulating film layer of claim 14, wherein the water-swellable filler comprises an organic filler.

16. The self-regulating film layer of claim 15, wherein the organic filler comprises a superabsorbent polymer.

17. The self-regulating film layer of claim 14, wherein the water-swellable filler comprises sodium bentonite.

18. The self-regulating film layer of claim 14, wherein the non-water-swellable filler comprises an inorganic filler.

19. A self-regulating multilayer breathable film, comprising:
    at least one self-regulating microporous breathable film layer including a voided matrix including a thermoplastic film-forming polymer and water-swellable filler selected from the group consisting of organic fillers, bentonite fillers and combinations thereof, within the voids; and
    at least one outer polymeric skin layer disposed on at least one side of the self-regulating microporous film layer;
    the multilayer film having an original WVTR of at least about 300 g/m$^2$/24 hours when the water-swellable filler is in a dry unswollen state and an WVTR less than about 70% of the original WVTR when the water-swellable filler is in a wet swollen state.

20. The self-regulating multilayer film of claim 19, wherein the outer skin layer has a thickness less than about 10 microns.

21. The self-regulating multilayer film of claim 19, wherein the outer skin layer has a thickness less than about 5 microns.

22. The self-regulating multilayer film of claim 19, wherein the outer skin layer has a thickness less than about 2.5 microns.

23. The self-regulating multilayer film of claim 19, wherein the water-swellable filler absorbs at least about 10 times its weight in distilled water.

24. The self-regulating multilayer film of claim 19, wherein the water-swellable filler absorbs at least about 20 times its weight in distilled water.

25. The self-regulating multilayer film of claim 19, wherein the water-swellable filler absorbs at least about 30 times its weight in distilled water.

26. The self-regulating layer of claim 19, comprising two of the outer polymeric skin layers disposed on both sides of the self-regulating microporous film layer.

27. The self-regulating layer of claim 19 wherein the WVTR is less than 50% of the original WVTR when the water-swellable filler is in a wet swollen state.

28. The self-regulating multilayer film of claim 19, wherein the water-swellable filler comprises an organic filler.

29. The self-regulating multilayer film of claim 28, wherein the organic filler comprises a superabsorbent polymer.

30. The self-regulating multilayer film of claim 19, wherein the water-swellable filler comprises sodium bentonite.

31. A self-regulating multilayer breathable film, comprising:
a self-regulating microporous breathable layer including a voided matrix including a thermoplastic film-forming polymer and a water-swellable filler selected from the group consisting of organic fillers, bentonite fillers and combinations thereof; and
at least one additional breathable polymeric layer disposed on one side of the self-regulating layer;
the multilayer film having an original WVTR of at least about 300 g/m²/24 hours when the water-swellable filler is in a dry unswollen state and a WVTR less than about 70% of the original WVTR when the water-swellable filler is in a wet swollen state.

32. The self-regulating multilayer film of claim 31, wherein the WVTR is less than 50% of the original WVTR when the water-swellable filler is in a wet swollen state.

33. The self-regulating multilayer film of claim 31, wherein the WVTR is less than 25% of the original WVTR when the water-swellable filler is in a wet swollen state.

34. The self-regulating multilayer film of claim 31, wherein the self-regulating layer comprises about 10–50% by weight of the water-swellable filler.

35. The self-regulating multilayer film of claim 31, wherein the water-swellable filler comprises bentonite clay.

36. The self-regulating multilayer film of claim 31, wherein the at least one additional layer comprises a second breathable layer including a second thermoplastic polymer matrix and a non-water-swellable filler dispersed within the second matrix.

37. The self-regulating multilayer film of claim 36, wherein the non-water-swellable filler constitutes about 10–70% by weight of the additional layer, and comprises an inorganic filler.

38. The self-regulating multilayer film of claim 36, wherein the second breathable layer is disposed adjacent to the self-regulating layer.

39. The self-regulating multilayer film of claim 38, further comprising a third polymeric layer adjacent the second breathable layer.

40. The self-regulating multilayer film of claim 36, wherein the water-swellable filler comprises a superabsorbent polymer and the non-water-swellable filler comprises calcium carbonate.

41. The self-regulating multilayer film of claim 31, wherein the self-regulating layer is thinner than the additional breathable polymeric layer.

42. The self-regulating multilayer film of claim 31, wherein the water-swellable filler comprises an organic filler.

43. The self-regulating multilayer film of claim 42, wherein the organic filler comprises a superabsorbent polymer.

44. A self-regulating microporous breathable fabric laminate, comprising:
at least one support layer; and
a self-regulating breathable film laminated to the support layer;
the self-regulating film including a self-regulating breathable microporous film layer which includes a voided polymer matrix and a water-swellable filler selected from the group consisting of organic fillers, bentonite fillers and combinations thereof, disposed within the matrix.

45. The laminate of claim 44, wherein the water-swellable filler has a dry unswollen state and a wet swollen state, and the film has an original WVTR of at least about 300 grams/m²/24 hours when the water-swellable filler is in the unswollen state and an WVTR less than about 70% of the original WVTR when the water-swellable filler is in the swollen state.

46. The laminate of claim 44, wherein the water-swellable filler comprises an organic filler.

47. The laminate of claim 46, wherein the organic filler comprises a superabsorbent polymer.

48. The laminate of claim 46, wherein the WVTR is less than 50% of the original WVTR when the water-swellable filler is in a the wet swollen state.

49. The laminate of claim 44, wherein the water-swellable filler comprises an inorganic filler.

50. The laminate of claim 49, wherein the WVTR is less than 50% of the original WVTR when the water-swellable filler is in a the wet swollen state.

51. The laminate of claim 44, wherein the self-regulating film comprises:
at least one self-regulating microporous breathable film layer including a voided matrix including a thermoplastic film-forming polymer and water-swellable filler within the voids; and
at least one outer polymeric skin layer disposed in at least one side of the self-regulating microporous film layer.

52. The laminate of claim 44, wherein the self-regulating film comprises:
a self-regulating microporous breathable layer including a voided matrix including a thermoplastic film-forming polymer and a water-swellable filler; and
a second microporous breathable layer disposed on at least one side of the self-regulating layer, the second breathable layer including a thermoplastic polymer matrix and a non-water-swellable filler.

53. The laminate of claim 44, wherein the support layer comprises a nonwoven web.

54. The laminate of claim 53, wherein the nonwoven web comprises a spunbonded web.

55. The laminate of claim 44, wherein the film and support layer are thermally bonded together.

56. The laminate of claim 44, wherein the film and support layer are bonded together using an adhesive.

57. The self-regulating fabric laminate of claim 44, wherein the water-swellable filler comprises an organic filler.

58. The self-regulating fabric laminate of claim 57, wherein the organic filler comprises a superabsorbent polymer.

59. The self-regulating fabric laminate of claim 44, wherein the water-swellable filler comprises sodium bentonite.

* * * * *